US006863666B2

(12) United States Patent
Minato

(10) Patent No.: US 6,863,666 B2
(45) Date of Patent: Mar. 8, 2005

(54) OPEN-TYPE DISPOSABLE DIAPER

(75) Inventor: Hironao Minato, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 137 days.

(21) Appl. No.: 10/310,439

(22) Filed: Dec. 5, 2002

(65) Prior Publication Data

US 2003/0114828 A1 Jun. 19, 2003

(30) Foreign Application Priority Data

Dec. 13, 2001 (JP) ..................................... 2001-380569

(51) Int. Cl.$^7$ ................................................ A61F 13/15
(52) U.S. Cl. ...................... 604/389; 604/386; 604/396; 604/394
(58) Field of Search .................................. 604/396, 387, 604/398, 389, 385.01, 385.21, 390, 391, 394, 386

(56) References Cited

U.S. PATENT DOCUMENTS

| 4,610,682 A | * | 9/1986 | Kopp | 604/385.21 |
| 4,911,702 A | * | 3/1990 | O'Leary et al. | 604/389 |
| 5,846,232 A | | 12/1998 | Serbiak et al. | |
| 5,873,870 A | | 2/1999 | Seitz et al. | |
| 6,544,244 B1 | * | 4/2003 | Glaug et al. | 604/389 |

FOREIGN PATENT DOCUMENTS

| EP | 0 547 497 A2 | 6/1993 |
| WO | WO 95/19753 | 7/1995 |
| WO | WO 96/21412 | 7/1996 |

* cited by examiner

Primary Examiner—Jacqueline Stephens
(74) Attorney, Agent, or Firm—Butzel Long

(57) ABSTRACT

An open-type disposable diaper is composed, in its longitudinal direction, of a crotch region, a front waist region and a rear waist region. The rear waist region is provided on its transversely opposite sides with wings and lobes extend outward from these wings in a transverse direction. These lobes are provided on inner surfaces thereof with fasteners. Each of the lobes is divided in a section placed aside toward an outer end and a section placed aside toward an inner end as viewed in the longitudinal direction. The section placed aside toward the outer end has an elastic stretchability in the transverse direction of the diaper higher than the section placed aside toward the inner end. The fastener is attached to the section placed aside toward the outer end.

3 Claims, 6 Drawing Sheets

OPEN-TYPE DISPOSABLE DIAPER

BACKGROUND OF THE INVENTION

This invention relates to disposable diapers for absorption and containment of excrements.

Conventional open-type disposable diapers generally comprise a front waist region, a rear waist region and a crotch region extending between these two waist regions. In many cases, the diaper is formed with wings defined by lateral extensions of transversely opposite side edges of the rear waist region and the wings are provided in the vicinity of lobes thereof with fasteners so that the fasteners may be detachably anchored on an outer surface of the front waist region when the diaper is put on a wearer's body.

In the case of the conventional diaper as has been described above, the fasteners are partially anchored on the outer surface of the front waist region with the lobes of the respective wings being tensioned in the waist-surrounding direction so as to ensure fitness of the diaper to the wearer's body. However, if the lobes are tensioned obliquely upward in the waist-surrounding direction, it will be difficult for the transversely opposite side edges of the diaper in the crotch region to be placed closely against the wearer's thighs. Consequently, there is a fear that leakage of excrements might occur along the thighs.

SUMMARY OF THE INVENTION

In view of the problem as has been described above, it is an object of this invention to improve the open-type disposable diaper so as to ensure the transversely opposite side edges of the diaper to be placed closely against the wearer's thighs as the diaper is put on the wearer's body.

According to this invention, there is provided an open-type disposable diaper having a transverse direction and a longitudinal direction, the diaper being composed, in the longitudinal direction, of a crotch region, a front waist region extending in front of the crotch region and a rear waist region extending behind the crotch region, one of the front and rear waist regions being provided on its transversely opposite side edges with wings and lobes extending outward from the wings in the transverse direction, the lobes being provided on inner surfaces thereof with fasteners adapted to be detachably anchored on an outer surface of the other of the front and rear waist regions.

Each of the lobes extending outward from the wings in the transverse direction is divided in two sections, one placed aside toward an outer end and the other placed aside toward an inner end as viewed in the longitudinal direction, the section placed aside toward the inner end being hard stretchable or non-stretchable outward in the transverse direction and the section placed aside toward the outer end being provided with the fastener.

According to one preferred embodiment of this invention, the lobes are formed to be more stretchable than outer end portions of the wings. According to another preferred embodiment of this invention, the section placed aside toward the outer end is non stretchable in its zone underlying the fastener.

DETAILED DESCRIPTION OF THE PREFERRED EMBODIMENTS

Details of an open-type disposable diaper will be more fully understood from the description given hereunder with reference to the accompanying drawings.

Figure 1:
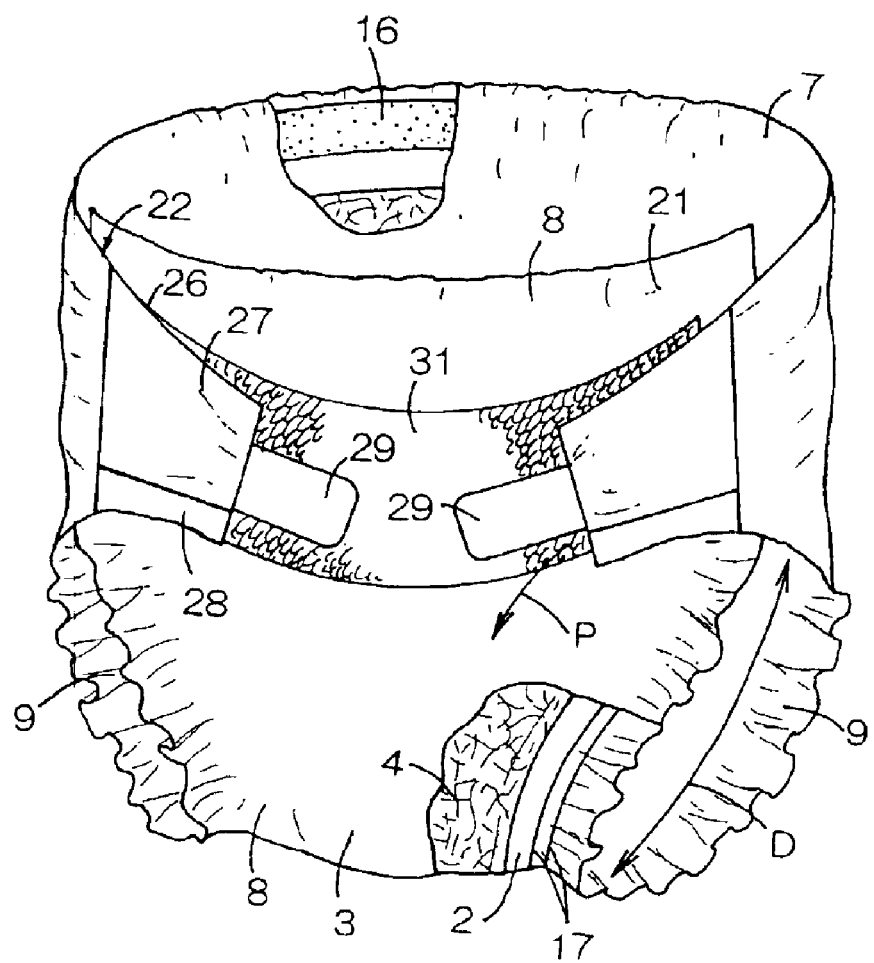
FIG. 1 is a partially cutaway perspective view showing a open-type disposable diaper according to this invention as the diaper put on a wearer's body.
Figure 2:
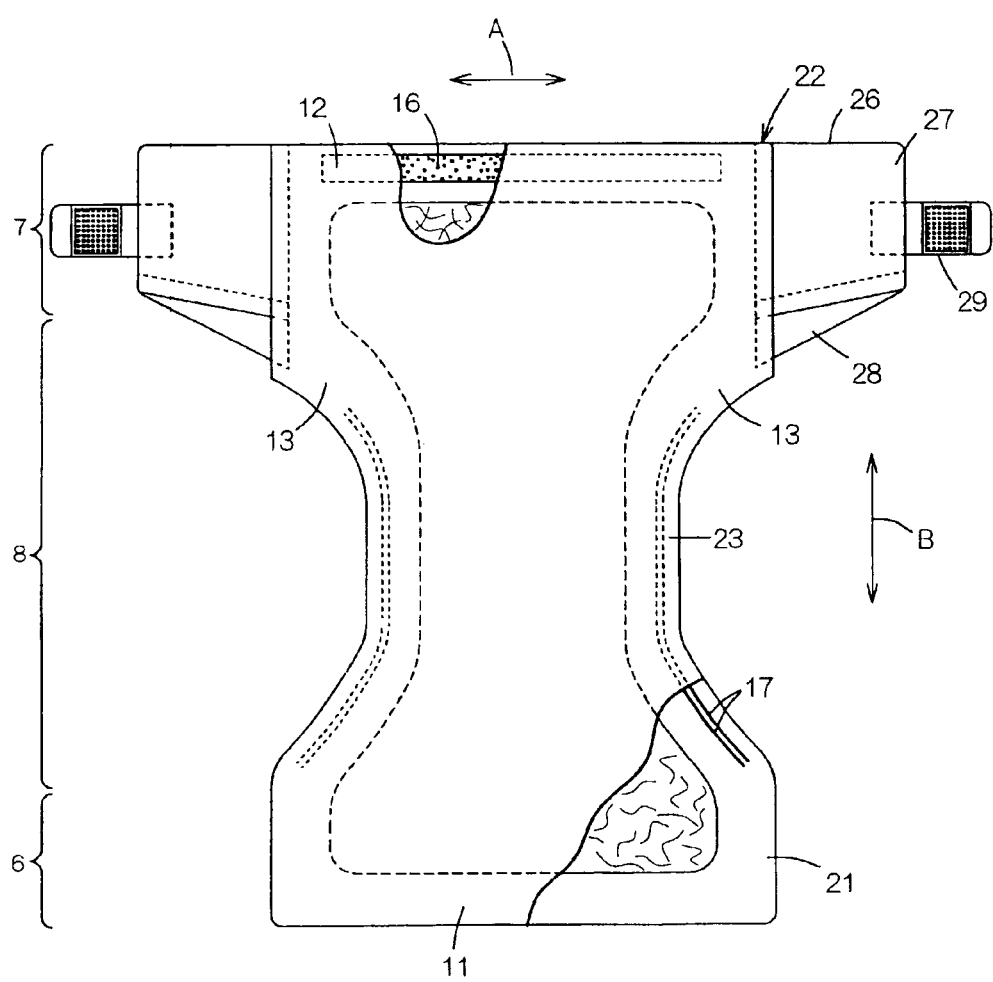
FIG. 2 is a partially cutaway plan view showing the disposable diaper of FIG. 1.

FIG. 1 is a partially cutaway perspective view showing the open-type disposable diaper 1 according to this invention as the diaper 1 put on a wearer's body and FIG. 2 is a partially cutaway plan view showing the disposable diaper 1 of FIG. 1. The diaper 1 having a transverse direction A and a longitudinal direction B comprises a liquid-pervious topsheet 2, a liquid-impervious backsheet 3 and a liquid-absorbent core 4 interposed between these two sheets 2, 3. Regarding its configuration, the diaper 1 is composed, in the longitudinal direction B, of a crotch region 8, a front waist region 6 extending in front of the crotch region 8 and a rear waist region 7 extending behind the crotch region 8. The top- and backsheets 2, 3 extend outward beyond a peripheral edge of the core 4 and put flat and joined together to form front and rear end flaps 11, 12 and right and left side edge flaps 13, 13. In the rear end flap 12 and the side edge flaps 13, 13, a waist-surrounding elastic member 16 and leg-surrounding elastic members 17, 17 are disposed between the top- and backsheets 2, 3 and secured in a stretched state to the inner surface of at least one of these sheets 2, 3. The side edge flaps 13 extend transversely outward, in the front and rear waist regions 6, 7, to form front wings 21 and rear wings 22 defining together lateral zones of the diaper 1 and describe, in the crotch region 8, circular arcs defining curved portions, respectively.

In the rear waist region 7 of the diaper 1, the respective rear wings 22 have lobes 26 extending outward therefrom in the transverse direction A. Each of these lobes 26 has a high stretchability section 27 placed aside toward its outer end and a low stretchability section 28 placed aside toward its inner end as viewed in the longitudinal direction B. The high stretchability section 27 is provided with a fastener 29. In the front waist region 6 of the diaper 1, the backsheet 3 is provided on its outer surface with a target section 31 on which the fastener 29 is detachably anchored. To put the diaper 1 on the wearer, e.g., infant, the lobes 26 of the respective rear wings 22 are pulled in the transverse direction A with the fasteners being held by fingers and the fasteners 29 are anchored on the target section 31. In this manner, the front wings 21 overlap the associated rear wings 22 to form leg-holes 9 each having a diameter D (See FIG. 1).

Figure 3:
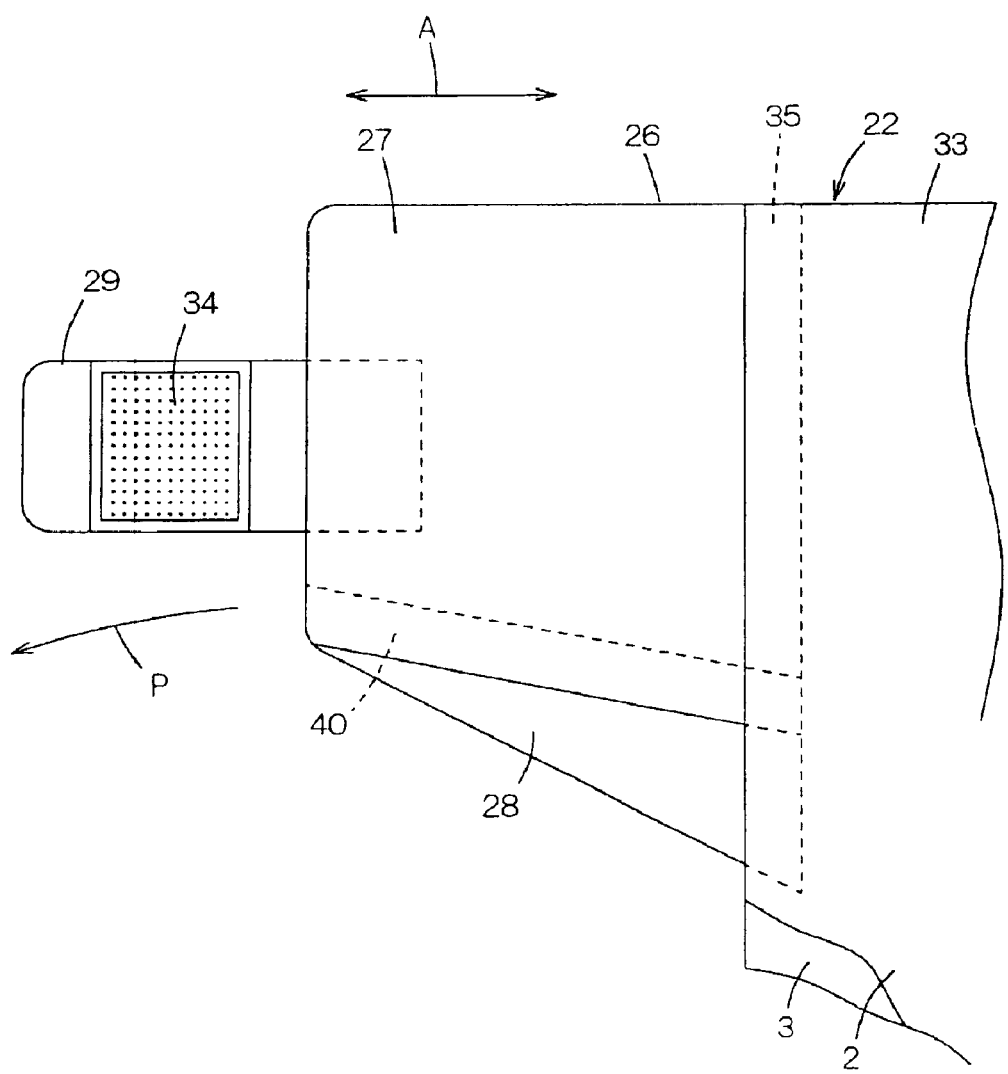
FIG. 3 is a fragmentary view of the disposable diaper.

FIG. 3 is a scale-enlarged view showing one of the rear wings 22 in the diaper 1. Each of the rear wings 22 has its outer end section 33 comprising the topsheet 2 and the backsheet 3 both being non-stretchable or elastically stretchable in the direction A. The lobe 26 overlaps the outer end section 33 of the associated rear wing 22 and joined to this along the overlapping zone 35. The lobe 26 comprises the high stretchability section 27 adapted to be easily elastically stretched in the transverse direction and the low stretchability section 28 adapted to be less easily stretched in the transverse direction A than the high stretchability section 27. Such high stretchability section 27 is made of a sheet material having elastic stretchability, such as a nonwoven fabric, plastic film or rubber sheet so that its stress at 5% stretch is at least 0.05 N per 25 mm width less than the stress at 5% stretch of the low stretchability section 28 as well as than the stress at 5% stretch of the outer end section 33. The low stretchability section 28 is made of a sheet material such as a nonwoven fabric or plastic film having no stretchability or an elasticity higher than that of the sheet material forming the high stretchability section 27. The sheet materials of these high and low stretchability sections 27, 28 are joined together along an overlapping zone 40 of these two sections. The fastener provided on the high stretchability section 27 is non-stretchable in the transverse direction A and has a fastening zone 34 on its inner surface. In the case of the fastener 29 in this illustrated embodiment, the fastening zone 34 is in the form of self adhesive or male member of so-called mechanical fastener traded, for example, as VELCRO provided on the inner surface of polyester resin tape.

With the rear wings 22 formed in such a manner, when the high stretchability sections 27 are pulled outward in the transverse direction A of the diaper 1 with the fasteners 29 hold by fingers, the free stretchability of the high stretchability sections 27 tending to stretch elastically is restricted by the low stretchability sections 28 positioned below so that the high stretchability sections 27 stretch in the direction shown by an arrow 9, i.e. obliquely downward as viewed in FIG. 3 and cause the rear wings 22 to form the leg-holes 9 each having a diameter D. That is, in the case of this diaper 1, when the rear wings 22 are pulled in the transverse direction A as the diaper 1 is put on a wearer's body, the leg-holes 9 become smaller so that the both side edge flaps 13 in the crotch region 8 are closely placed against the wearer's thighs and there is no fear that leakage of excrements might occur along the thighs. The target zone 31 presents U- or V-shape in its plane view (See FIG. 1) as the rear wings 22 are pulled downward and thereby facilitates the fasteners 29 to be anchored on the target zone 31. Such target zone 31 is formed of plastic film if the fastening zones 34 are made of adhesives and formed of the female member of so-called mechanical fastener if the fastening zones 34 are provided in the form of the mechanical fastener's male members.

Figure 4:
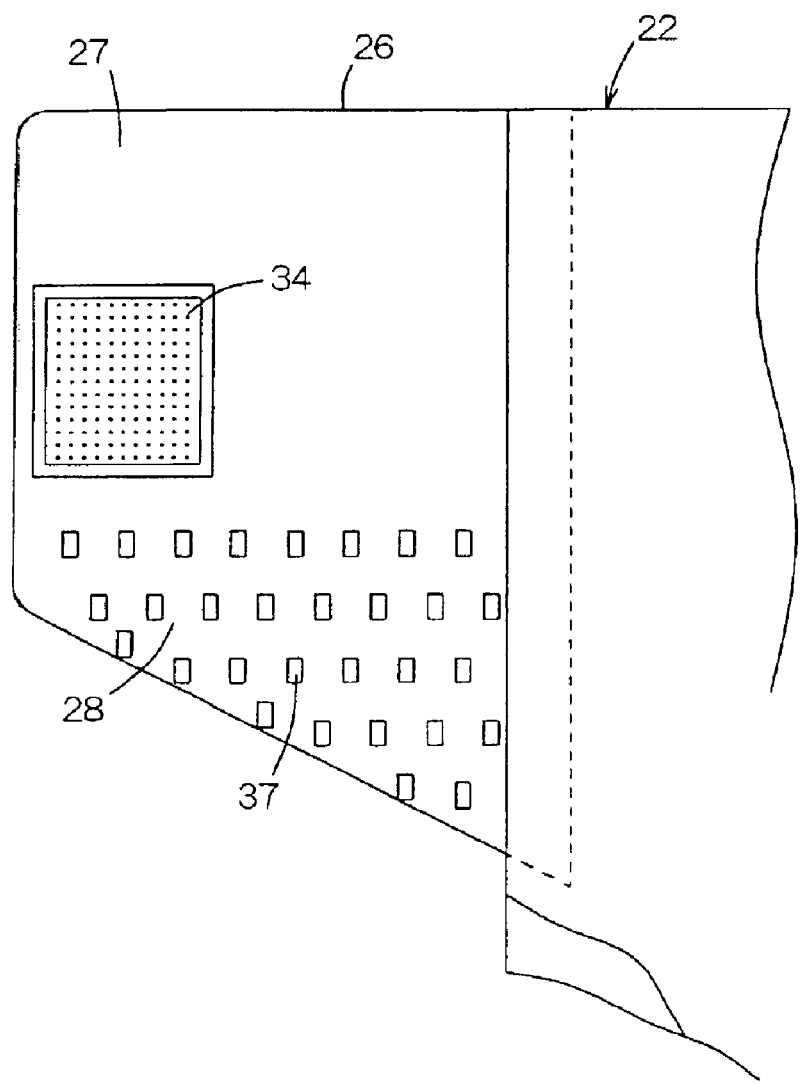
FIG. 4 is a view similar to FIG. 3 showing one preferred embodiment of the disposable diaper according to this invention.

FIG. 4 is a view similar to FIG. 3 showing one preferred embodiment of the disposable diaper according to this invention. In this diaper 1, each of the lobes 26 extending outward from the rear wings 22 in the transverse direction is formed by a single sheet of elastically stretchable nonwoven fabric, for example, made of styrene-based elastomeric fibers. This nonwoven fabric has a plurality of film-like spots 37 distributed on its lower section which has been thermally treated under appropriate pressure to form these film-like spots 37. This lower section is less stretchable than the upper section of the lobe 26 as viewed in FIG. 4. In other words, the lower section corresponds to the low stretchability zone 28 and the upper section corresponds to the high stretchability zone 27 in the embodiment illustrated by FIG. 2. The male member of the mechanical fastener is joined to the inner surface of the high stretchability zone 27 to form the fastening zone 34. It should be understood that the portion of the high stretchability zone 27 underlying the male member is non-stretchable.

Figure 5:
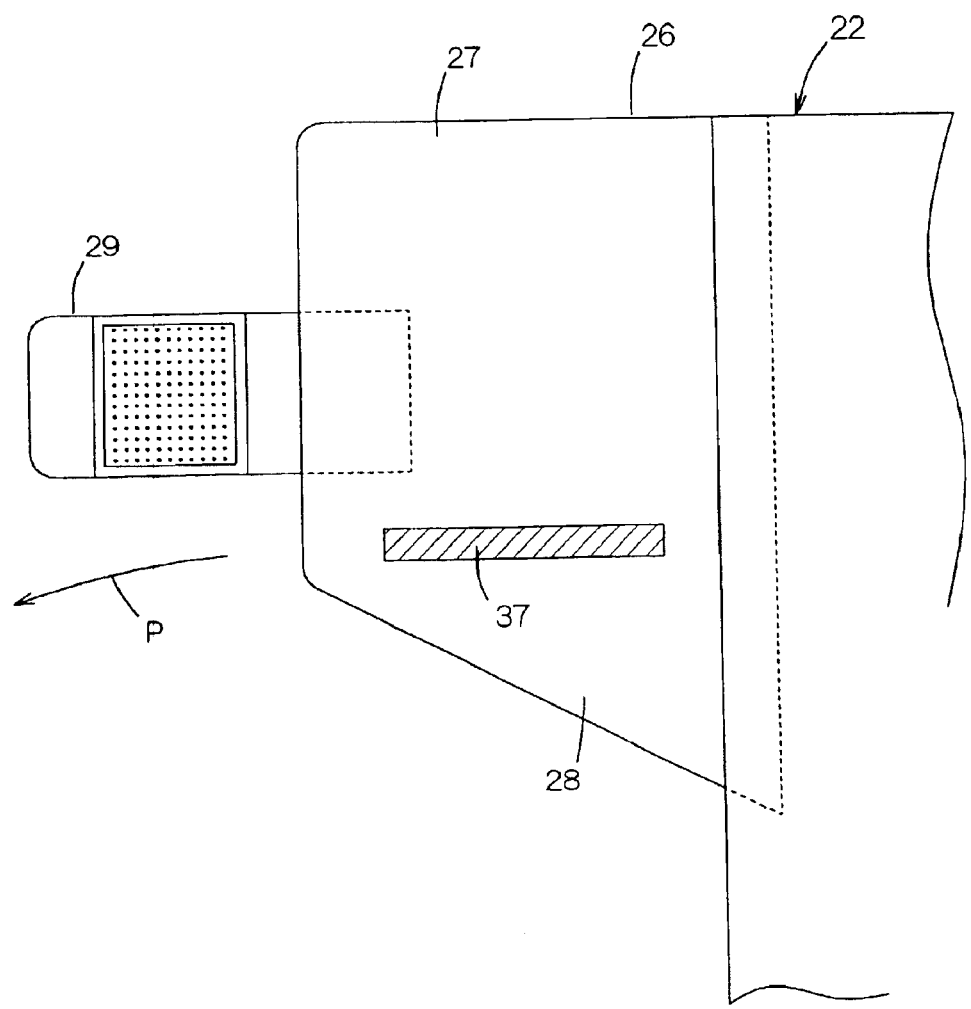
FIG. 5 is a view similar to FIG. 4 showing another preferred embodiment of the disposable diaper according to this invention.

FIG. 5 is a view similar to FIG. 4 showing another preferred embodiment of the disposable diaper 1 according to this invention. Also in this embodiment, each of the lobes 26 extending outward from the rear wings 22 in the transverse direction A is formed by a single sheet of elastically stretchable nonwoven fabric. The lobe 26 is at least partially divided in upper and lower sections by a film-like zone 37 extending in the transverse direction A so that the upper section may function as the high stretchability zone 27 and lower section extending below the zone 37 may function as the low stretchability zone 28. When the fastener 29 is pulled outward in the transverse direction A, the high stretchability zone 27 can be easily stretched but the low stretchability zone 28 is restrained by the zone 37 from being stretched in the same manner as the high stretchability zone 27. Consequently, in the case of the rear wings 22 according to this embodiment also, the high stretchability zones 27 are stretched in the direction indicated by the arrow P as in the embodiment illustrated by FIG. 3.

Figure 6:
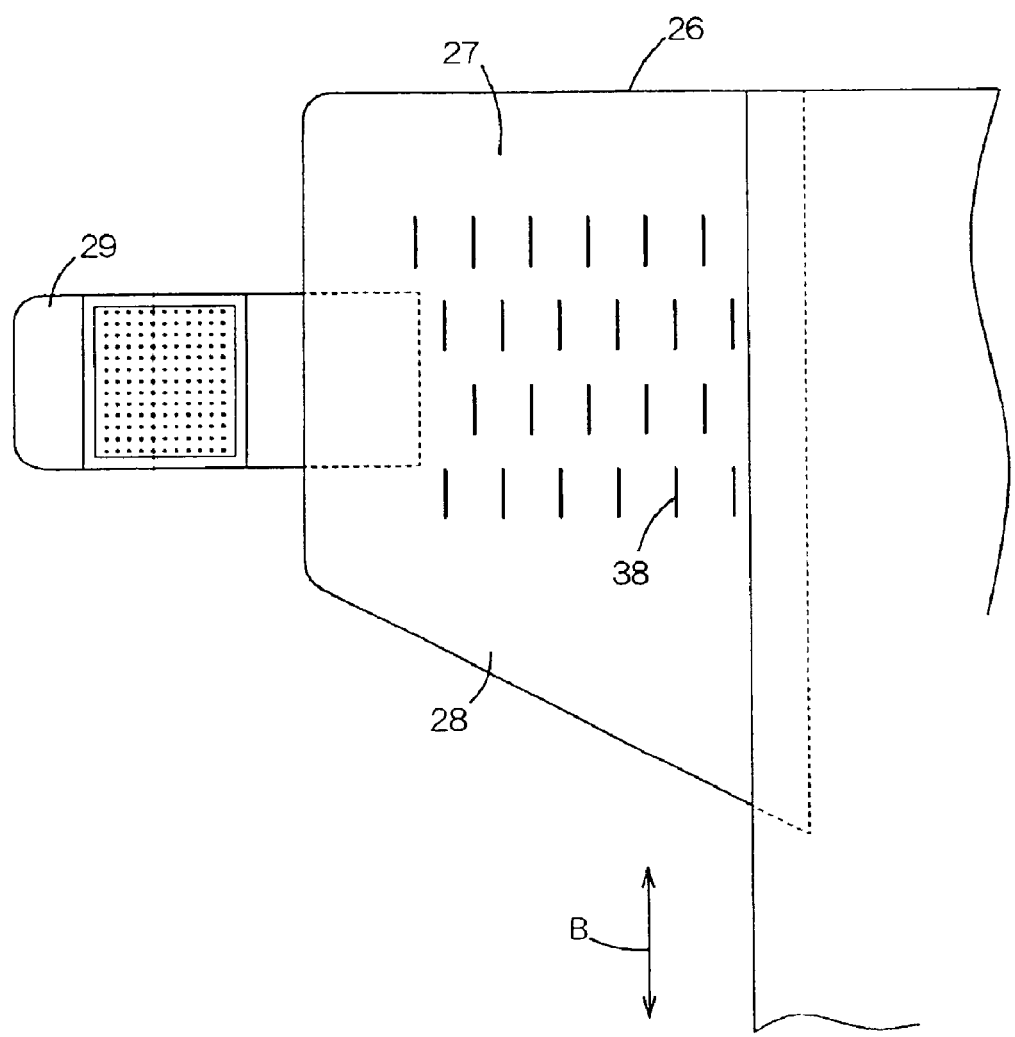
FIG. 6 is a view similar to FIG. 5 showing still another preferred embodiment of the disposable diaper according to this invention.

FIG. 6 is a view similar to FIG. 5 showing still another preferred embodiment of the disposable diaper 1 according to this invention. Also in this embodiment, each of the lobes 26 extending outward from the rear wings 22 in the transverse direction A is formed by a single sheet of elastically stretchable nonwoven fabric. The lobe 26 is formed in its upper section with a plurality of slits 38 each extending in the longitudinal direction B. The presence of the slits 38 permits the upper section of the lobe 26 to be more easily stretched in the transverse direction A of the diaper 1 than the lower section having none of such slits 38 and thereby permits the lobe 26 to behave in the same manner as the lobe 26 according to the embodiment illustrated in FIG. 3. In this lobe 26 also, the upper section functions as the high stretchability zone 27 and the lower section functions as the low stretchability 28.

Without departing from the spirit and the scope of this invention, it is possible to provide the high stretchability zone and the low stretchability zone in each of the front wings 21 instead of providing the zones in each of the rear wings 22 and to provide the target zone in the rear waist region 7 instead of providing this in the front waist region 6. While each of the front wings 21 is illustrated to have a dimension in the waist-surrounding direction smaller than that of the rear wing 22, it is also possible to enlarge the front wings 21 to the dimension of the rear wings 22.

The open-type disposable diaper according to this invention is primarily characterized in that each of the lobes extending outward from the front or rear wings in the front or rear waist region in the transverse direction is formed with the high stretchability zone and the low stretchability zone wherein the fastener is attached to the inner surface of the lobe in its high stretchability zone. Such feature ensures that the leg-holes of the diaper have the diameters reliably reduced to come in close contact with the wearer's thighs as the fasteners are pulled in the transverse direction of the diaper to put it on the wearer's body.

What is claimed is:

1. An open-type disposable diaper having a transverse direction and a longitudinal direction, said diaper being composed, in said longitudinal direction, of a crotch region, a front waist region extending in front of said crotch region and a rear waist region extending behind said crotch region, one of said front and rear waist regions being provided on its transversely opposite side edges with wings and lobes extending outward from these wings in said transverse direction, said lobes being provided on inner surfaces thereof with fasteners adapted to be detachably anchored on an outer surface of the other of said front and rear waist regions, said open-type disposable diaper further comprising:

each of said lobes extending outward from said wings in the transverse direction being divided in two sections, one placed aside toward an outer end and the other placed aside toward an inner end as viewed in said longitudinal direction, said section placed aside toward the inner and being hard stretchable or non-stretchable outward in said transverse direction and said section placed aside toward the outer end being provided with the fastener, said two sections of each of said lobes having adjacent longitudinal edges which are substantially coextensive in the transverse direction.

2. The disposable diaper according to claim 1. wherein said lobes are formed to be more stretchable than outer end portions of said wings.

3. The disposable diaper according to claim 1, wherein said section placed aside toward the outer end is non-stretchable in its zone underlying said fastener.

* * * * *